United States Patent [19]
Belletti

[11] Patent Number: 5,872,103
[45] Date of Patent: Feb. 16, 1999

[54] PREVENTION OF MAMMARY TUMORS BY TREATMENT WITH CARDIAC GLYCOSIDES

[76] Inventor: Dino A. Belletti, 47 Shore Rd., Manhasset, N.Y. 11030

[21] Appl. No.: 672,144

[22] Filed: Mar. 19, 1991

Related U.S. Application Data

[63] Continuation of Ser. No. 511,808, Apr. 17, 1990, abandoned, which is a continuation of Ser. No. 935,443, Nov. 26, 1986, abandoned.

[51] Int. Cl.$^6$ ..................................................... A61K 31/70
[52] U.S. Cl. ................................................... 514/26; 536/5
[58] Field of Search .................................... 514/26; 536/5

[56] References Cited

PUBLICATIONS

Li et al., *Chemical Abstract* vol. 88 (1), 1978 p. 15 No. 166a.

*Primary Examiner*—Elli Peselev
*Attorney, Agent, or Firm*—Pennie & Edmonds

[57] ABSTRACT

Methods for the prevention of neoplasms by treatment with cardiac glycosides are described. Individuals at a high risk of developing neoplasia or cancer may be treated with a therapeutically effective dose of a cardiac glycoside prophylactically. Individuals who convert cardiac glycosides to inactive metabolites may be treated with a modified regimen which prevents inactivation of the drug.

33 Claims, No Drawings

PREVENTION OF MAMMARY TUMORS BY TREATMENT WITH CARDIAC GLYCOSIDES

This application is a continuation of application Ser. No. 07/511,808 filed Apr. 17, 1990 (abandoned), which is a continuation of application Ser. No. 06/935,443 filed Nov. 26, 1986 (abandoned).

TABLE OF CONTENTS
1. Introduction
2. Background of the Invention
   2.1. Chemical Nature and Properties of the Cardiac Glycosides
   2.2. Pharmacokinetics of the Cardiac Glycosides
   2.3. Cardiac Glycosides and Cancer
   2.4. Cancer Prevention
3. Summary of the Invention
4. Detailed Description of the Invention
   4.1. Choice of Cardiac Glycoside Treatment and Dosage
   4.2. Identifying Patients With a High Risk of Developing Cancer
   4.3. Identification and Treatment of Converters
Example: Prevention of Neoplasia by the Administration of Digoxin
   5.1. Treatment of Mice
   5.2. Results of Treatment

1. INTRODUCTION

The present invention is directed to methods for the prevention of neoplasms by treatment with cardiac glycosides. The method of the invention involves treating an individual at a high risk of developing neoplasia or cancer with a therapeutically effective dose of a cardiac glycoside prophylactically. Individuals who convert cardiac glycosides to inactive metabolites can be treated with a modified regimen to prevent inactivation of the drug.

The invention is illustrated, by way of example, using a murine model which demonstrates the effectiveness of the cardiac glycoside, digoxin, in the prevention of mammary neoplasms.

2. BACKGROUND OF THE INVENTION

Since the publication of "An Account of the Fox Glove and Some of its Medical Uses; with Practical Remarks in Dropsy, and other Diseases" by William Withering over two hundred years ago, the usefulness of digitalis has been in the area of cardiovascular diseases. Whether it is for the control of cardiac arrythmias or for its inotropic effect on the failing heart, the cardiac glycosides have an established role in treating heart disease.

Cardiac glycosides are found in a number of plants, and a few are present in the venom of certain toads. Cardiac glycosides have been found in twelve plant families including the dogbone family (Apocyanaceae), the figwort family (Serophulariaceae) the lily family (Liliaceae), the mulberry family (Moraceae) and the buttercup family (Ranunculaceae). The main source is Digitalis spp. Recently, cardiac glycosides have also been found in insects such as grasshoppers and butterflies which take them up in their vegetable diet. The term "digitalis" as used herein designates the entire group of cardiac glycosides rather than only those obtained from digitalis.

2.1. Chemical Nature And Properties Of The Cardiac Glycosides

Each member of the cardiac glycosides comprises an aglycone or genin with from one to four molecules of sugar. The aglycones are steroids characterized by an unsaturated five-or six-membered lactone ring attached to C17. Glycosides with a five-membered lactone ring are classified as cardenolides (eg., strophanthidine and digitalis glycosides) and those with a six-membered lactone ring as bufadienolides. The sugar components of the glycosides are attached to the C3 hydroxyl group of the aglycone:

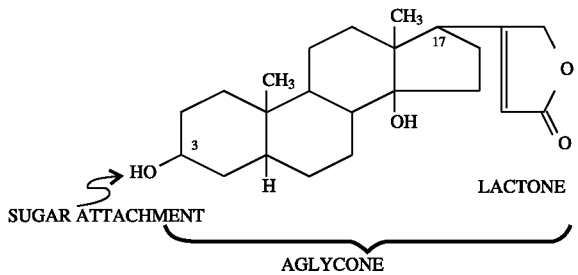

Pharmacological activity of the cardiac glycosides resides in the aglycone whereas the sugar component modifies water and lipid solubility and, therefore, distribution and potency of the drug. Saturation of the lactone ring reduces activity by tenfold or more and opening of the lactone ring completely abolishes activity. (See Goodman and Gilman eds., 1980, The Pharmacological Basis Of Therapeutics, 6th Edition, Ch. 30, pp. 729–760).

Digitalis is used almost exclusively for two purposes—either to restore an adequate circulation in patients with congestive heart failure or to slow ventricular rate in patients with atrial fibrillation or flutter. The mechanisms responsible for the beneficial effects of digitalis are complex. Digitalis exerts direct effects on the heart that modify both its mechanical and electrical activity. Similarly, it acts directly on smooth muscle of the vascular system. In addition, digitalis exerts a number of effects on neural tissue and, thus, indirectly influences the mechanical and electrical activity of the heart, and modifies vascular resistance and capacitance. The most probable explanation for the direct positive inotropic effect is the ability of digitalis to inhibit the membrane-bound $Na^+,K^+$-activated adenosine triphosphatase ($Na^+,K^+$-ATPase) which is coupled to the cellular sodium-potassium pump that is responsible for extrusion of $Na^+$ from the cell and transport of $K^+$ into the cell. Digitalis glycosides bind specifically to the $Na^+,K^+$-ATPase, inhibit its enzymatic activity, and impair the active transport of $Na^+$, and $K^+$. Although the mechanism by which digitalis potentiates excitation-contraction coupling is unknown, it is postulated that the $Na^+,K^+$-ATPase inhibition results in an increase in intracellular $Na^+$ and decrease in intracellular $K^+$; because cardiac fibers possess a mechanism for the exchange of intracellular $Na^+$ for extracellular $Ca^{++}$ the augmented exchange results in an influx of $Ca^{++}$. It is believed that the contraction of mammalian hearts is initiated by the influx of $Ca^{++}$ (see Goodman & Gilman, 1980, The Pharmacological Bases Of Therapeutics, 6th Edition at pp. 732–734).

2.2. Pharmacokinetics Of The Cardiac Glycosides

The cardiac glycosides in predominant clinical use, digoxin and digitoxin, are available for oral or intravenous administration. Once administered, the digitalis glycosides are distributed to most body tissues, including red blood cells, skeletal muscle and heart. At equilibrium, the concentrations in cardiac tissues are 15 to 30 times those in plasma. Binding to tissue is decreased by an increase in the extracellular concentration of potassium. Digoxin is eliminated primarily by the kidney. Digitoxin is actively metabolized by the hepatic microsomal enzymes; one of the products is digoxin.

A few patients form cardioinactive metabolites of digoxin, in which case it is almost impossible to obtain a cardio-therapeutic effect. In these patients, digoxin undergoes biotransformation to dihydrodigoxin and its corresponding aglycone, dihydrodigoxigenin. These two relatively cardio- inactive metabolites, referred to as digoxin reduction products, appear to be made exclusively by bacteria in the gastrointestinal tract, probably the colon. The digoxin reduction products are absorbed through the gastrointestinal tract and eventually enter the systemic circulation. Such conversion cannot be avoided by non-oral routes of administration of the drug in these patients because digoxin is secreted into the gastrointestinal tract via the entero-hepatic circulation, converted to the reduction product and reabsorbed so that the reduction product enters the systemic circulation. Therapy with certain antibiotics causes disappearance of the reduced metabolites from the stool and urine, which can lead to increased bioavailability of the drug; alternatively administration of digoxin in capsule form which allows more complete absorption of digoxin in the small intestine decreases the percent of digoxin reduction products formed (see, Marcus, 1985, J. Am. Coll. Cardiol. 5 (5): 82A–90A; Dobkin et al., 1982, Science 220: 325–327; Lindenbaum, et al., 1981, Am. J. Med. 71: 67–74; Lindenbaum, et al., 1981, N. Eng. J. Med. 305: 789–794).

2.3. Cardiac Glycosides And Cancer

The toxic nature of cardiac glycosides led a few investigators to examine the effects, if any, of cardiac glycosides on neoplastic cells. Shiratori (1967, GANN 58: 521–528) assessed the cytotoxic effect of cardenolides on HeLa-$S_3$ cells, and found a high correlation between cytotoxicity in vitro and cardiac activity. However, when tested for antitumor activity, the cardenolides which exhibited high cytotoxicity against cultured cells showed no inhibitory effect whatsoever against the growth of Ehrlich ascites carcinoma cells even when the maximum tolerance dose was employed.

Williams, et al. (1976, Am. J. Med. Sci. 272(2): 132–137) examined the uptake of digoxin by central nervous system neoplastic tissues known to have differential contents of $Na^+,K^+$-ATPase. Digoxin uptake was found to be significantly lower in the more malignant central nervous system tumors.

Stenkvist, et al. (1979, Analyt. Quant. Cytol. 2: 49–54; The Lancet, Mar. 10, 1979, p. 563) explored possible correlations between the use of cardiac glycosides and the morphology of breast cancer. A comparison of patients who used cardiac glycosides to those who did not revealed no significant correlation between the use of cardiac glycosides and the occurrence of breast cancer. However those patients using cardiac glycosides who developed breast cancer, did so with a tumor cell population consisting of cells that were smaller and more uniform in morphology, density and size than those of patients not using cardiac glycosides. In addition, the tumor volume was smaller at diagnosis and the later distant spread and recurrence of breast cancer was reported to be lower in patients on digitalis medication (Stenkvist, et al., The New Engl. J. Med., Feb. 25, 1982, p.484 ; see also Goldin and Safa, The Lancet, May 19, 1984, p.1134). Stenkvist, et al. proposed that digitalis, having a steroid structure similar to that of estrogenic hormones, interferes with estrogen receptors in some way. LeWinn (The Lancet, Jun. 2, 1979, pp. 1196–1197) who also reported an estrogen-like effect of digitalis, namely gynaecomasta (inducement of a greater amount of breast tissue than normal) in men and post menopausal women using digoxin, cautioned that in some circumstances digoxin compounds may have an exacerbating effect on breast cancer and suggested that more information regarding the patient population used by Stenkvist, et al. was required.

In contrast to the postulate of Stenkvist, et al., Cove and Barker (The Lancet, Jul. 28, 1979, p. 204) reported that digoxin did not interfere with the binding of estrogen or progesterone to breast carcinoma cells in vitro, and suggested that it is unlikely that digoxin has any direct action on the binding of these hormones to receptors on breast cancer cells in vivo. This interpretation was shared by Falconer, et al. (1983, Chemotherapy 29: 368–372) who additionally reported a rapid decrease in DNA synthesis (as measured by $^3$H-thymidine incorporation) in human breast tumor tissue cultured in the presence of 100–200 ng/ml digoxin. However, no statistically significant effect on DNA synthesis was observed in the presence of 1–2 or 10–20 ng/ml digoxin which is closer to a "therapeutic" plasma concentration (see Goodman and Gilman, eds., 1980 The Pharmacological Basis of Therapeutics, 6th Edition, Table 30–1 at p. 748 which expresses 0.5–2.0 ng/ml as the range for a "therapeutic" plasma concentration for digoxin).

In the recent past the reports of Stenkvist, et al. and Goldin and Safa (supra) have been met with criticism. Friedman (The Lancet, Oct. 13, 1984 p.875) reported that no negative or inverse relation between digitalis and subsequent breast cancer was observed in a study of 143,594 people whose pharmacy records had been computer stored. Indeed, digitalis was reported to be positively associated with risk of cancer of the colon, lungs and prostate. Friedman suggested that the prior reports did not use appropriate comparison groups and concluded that digitalis does not appear to prevent breast cancer from occurring or being diagnosed, but leaves open the question of whether digitalis slows the growth of breast cancer once the cancer is present.

2.4. Cancer Prevention

According to the American Cancer Society (see "Cancer Facts and Figures", 1986, American Cancer Society) some cancers can be prevented by avoiding their causes. Primary prevention refers to steps that may be taken to avoid those factors that might lead to the development of cancer. For example, most lung cancers are caused by smoking and most skin cancers by frequent over-exposure to sun light. Other cancers are caused by occupational-environmental factors (e.g., nickel, chromate, asbestos, vinyl chloride, etc.). In addition, proper nutrition has increasingly become recognized as important for primary cancer prevention. High-fat diets have been implicated as a factor in the development of certain cancers such as breast, colon and prostate. High-fiber foods may help reduce the risk of colon cancer. Foods rich in vitamins A and C may help lower the risk for cancers of the larynx, esophagus and lung. Salt-cured, smoked and nitrite-cured foods have been linked to esophageal and stomach cancers. The heavy use of alcohol, especially accompanied by cigarette smoking or chewing tobacco increases the risk of cancers of the mouth, larynx, throat, esophagus and liver.

Secondary prevention refers to steps taken to diagnose a cancer or precursor as early as possible after it has developed so that a proper therapeutic course of action can be prescribed. For certain cancers, such as colorectal cancer, breast cancer and uterine cancer, early detection is of key importance.

Currently, chemoprevention studies with agents like synthetic retinoids, beta-carotene, folic acid and other vitamins and minerals are being undertaken to see if recurrences of cancers can be prevented. It remains to be seen whether any of these agents would be effective in primary prevention of cancer in an individual. In fact, it would be greatly advantageous if a therapy or treatment could be developed that would afford primary protection against factors that might lead to the development of cancer.

3. SUMMARY OF THE INVENTION

The present invention is directed to a method for the prevention of neoplasms which involves using a cardiac glycoside prophylactically to treat an individual who is at risk of developing a neoplasm prior to the development of a tumor in vivo. Accordingly, an effective dose of a cardiac glycoside is administered to and maintained in an individual who has a high risk of developing a neoplasm but, who has not yet developed a tumor. Therapy with a cardiac glycoside should be commenced prior to the individual's exposure to an agent that causes the cancer or the transforming event.

If the individual converts the cardiac glycoside to an inactive reduced product (eg., via biotransformation of the cardiac glycoside to an inactive metabolite) the individual should be treated prior to and/or during the administration of the cardiac glycoside in order to eliminate or minimize the conversion. For example, concurrent therapy with certain antibiotics can be used to eliminate the conversion where reduction products are made exclusively by bacteria in the gastrointestinal tract. Alternatively, the cardiac glycoside can be administered as an oral dose formulated so that more complete absorption occurs in the small intestine in order to decrease the percent of inactive reduction products formed.

The method of the invention is demonstrated by way of example, using a murine model in which therapy with digoxin completely prevented the formation of mammary tumors. The invention is based, in part, on the discovery that digoxin, contrary to prior observations of no correlation between cardiac glycosides and the occurrence of cancer, was able to completely prevent the development of mammary tumors in a strain of female mice which are highly susceptible to the development of such tumors. The invention is also based, in part, upon the discovery that digoxin treatment was not effective in preventing mammary tumors in female mice which formed digoxin reduction products and that such individuals require a regimen that prevents conversion of the drug.

4. DETAILED DESCRIPTION OF THE INVENTION

The method of the invention involves administering and maintaining an effective dose of a cardiac glycoside to an individual who is identified as being at risk of developing cancer but has not yet developed a neoplasm, in order to prevent neoplasia. The results of experiments described in the examples herein indicate that the cardiac glycoside, and not its reduced inactive metabolites, should be administered to the individual prior to exposure to the agent that causes the cancer whether it be a virus, chemical, or ionizing radiation or prior to the transforming event.

While the applicant is under no duty or obligation to explain the mechanism by which the invention works, it may be that the change in membrane potential resulting from the ability of the cardiac glycoside to bind to and inhibit the cellular membrane-bound $Na^+,K^+$-ATPase may prevent malignant transformation by any of a number of mechanisms. For example, the change in membrane potential may interfere with replication, inhibit carcinogens from crossing the cell membrane, or interfere with the transformation event normally induced by carcinogens.

In general, three different types of agents are known to be responsible for malignant transformation of cells: viruses, chemicals and radiation. Each type of influence is recognized as a carcinogen (a cancer-causing agent).

In animals, a number of tumors have been shown to be caused by viruses. In certain specific situations, human tumor viruses have been found, a number of which have been implicated in human cancers. Such tumor viruses include, but are not limited to Epstein-Barr Virus, a herpes-like DNA virus that probably plays a role in Burkitt's lymphoma and nasopharyngeal carcinoma; human retroviruses such as human T-cell leukemia virus which is associated with a T-lymphocytic tumor; hepatitis B virus, a small DNA virus that is correlated with liver cancers; and papilloma viruses, small DNA viruses responsible for warts that are associated with human cervical carcinoma.

In general, tumor viruses cause malignant transformation as a consequence of their ability to integrate their genetic information into the host cell DNA. Most often they cause chronic production of one or more proteins called transforming proteins, which are responsible for maintaining the transformed state of the infected cells. These transforming proteins are synthesized by the cell machinery under the direction of transforming genes in an integrated viral genome. For DNA tumor viruses, the known transforming genes are integral parts of the viral genome. By contrast, for RNA tumor viruses (i.e., retroviruses) the transforming genes are normal cellular genes (called protooncogenes) or slightly modified cellular genes that are either appropriated from the host cell and acquired by the retrovirus or hyperactivated in the host cell by the insertion of viral elements nearby. In either case the appropriated or hyperactivated genes become cancer-inducing genes called oncogenes. The acquisition of an oncogene by a transmissible retrovirus, however, is a low-probability event because the resulting virus is defective and depends on a helper virus for cell to cell transmission. In natural populations, hyperactivation of the oncogene by insertion and integration of a retrovirus promoter or enhancer is probably the major cause of retrovirus-induced cancer.

It may be that treatment of an individual with a cardiac glycoside in accordance with the invention prevents infection and/or interferes with integration of tumor virus genomes into the cell via the inhibition of the membrane-bound $Na^+,K^+$-ATPase which ultimately affects the transmembrane potential of the cell membrane. As an alternative explanation for tumor prevention, it may be that the inhibition of the $Na^+,K^+$-ATPase creates ion channels which, in turn, affect the ability of viral promoters or enhancers to induce the expression of oncogenes.

While viruses probably cause a few human cancers, chemical carcinogens are thought to be the causative factor in a larger number of cases. Chemical carcinogens react with and modify cellular DNA and cause permanent changes in DNA and therefore, are mutagens. There are two broad categories of chemical carcinogens: direct acting and indirect acting. Direct acting chemical carcinogens, which are few in number, are reactive electrophiles (compounds that seek out and react with negatively charged centers in other compounds). By contrast, indirect acting chemical carcinogens are metabolically converted to reactive electrophiles. The metabolic activation is carried out by enzymes that are normally resident in the body, especially in the liver which detoxifies noxious chemicals by adding hydrophilic groups to toxic insoluble compounds in order to render them soluble so that they can be eliminated. The detoxification process begins with a powerful series of reactions catalyzed by a set of enzymes, cytochrome P-450s, which are bound to endoplasmic reticulum membranes, and can oxidize even highly unreactive compounds to form epoxides which are very reactive electrophilic groups. Whether a chemical is a direct or indirect carcinogen, once inside a cell the electrophiles can react with negatively charged centers in DNA, RNA, proteins, etc. which can cause mutations and result in the formation of cellular oncogenes, i.e., mutated genes that are resident in cellular chromosomes. A few cellular oncogenes from human tumor cells have been cloned and sequenced. The human oncogenes sequenced to date are related to the c-ras family. The cellular ras oncogene (derived from human bladder carcinoma) differs from the normal c-ras protooncogene by a single nucleotide that causes a single amino acid change. Cellular oncogenes have been identified in tumors of the bladder, lung, breast, large intestine and neural tissue as well as in leukemias. For example, the abl oncogenes, which encode tyrosine specific protein kinases are found in chronic myelogenous leukemia; the neu oncogenes, which encode a receptor-like tyrosine specific protein kinase, are found in neuroblastoma; the ras oncogenes, which encode guanine nucleotide-binding proteins with GTPase activity (p21 proteins) are found in bladder, mammary, skin, lung and colon carcinomas as well as neuroblastoma leukemias; and the myc oncogenes which encode nuclear proteins that are possibly involved in regulating transcription are found in neuroblastoma and leukemia.

It may be that treatment of an individual with a cardiac glycoside in accordance with the invention prevents entry of a carcinogen into a cell because of the effect of the drug on transmembrane potential of the cell which may render the cell impermeable to the carcinogen. Alternatively, the change in the intracellular ionic environment induced by the cardiac glycosides which inhibit the cellular membrane-bound $Na^+$, $K^+$-ATPase may have an impact on the reactive electrophilic centers of the carcinogenic chemicals that may interfere with their activity. Another mechanism which may account for the tumor preventive effect of cardiac glycosides may involve alterations in cellular ion channels caused by inhibition of the membrane-bound $Na^+,K^+$-ATPase which, in turn, may affect the induction of expression of cellular oncogenes. Interestingly, a recent report (Morgan and Curran, 1986, Nature 322: 552–555) described the induction of expression of the protooncogene c-fos by conditions that effected voltage—dependent calcium channels. This provides evidence that the expression of protooncogenes, and perhaps cellular oncogenes, may be controlled or induced through ion channels. It is quite possible, therefore, that the mechanism responsible for the effect of the cardiac glycosides in the prevention of tumors as demonstrated in the examples infra may be due to the ability of the cardiac glycosides to bind to and inhibit the membrane bound $Na^+,K^+$-ATPase which alters the ionic flux of the cell membrane. Such inhibition of the $Na^+,K^+$-pump may prevent ion flux-induced expression of a protooncogene or an oncogene.

The principles discussed above are supported by the murine model presented in the examples infra in which the development of mammary tumors was prevented by treatment with digoxin in mice that are genetically susceptible to developing mammary tumors. These inbred mouse strains have extremely high incidences of mammary carcinoma that appears at an early age (5–12 months). This unique property is continuously transferred from generation to generation as the result of milk-borne virus combined with a suitable host genotype; in fact, it has been concluded that the virus in some mouse substrains of C3H could be transmitted to the offspring at conception by either parent Bentvelzen and Hilgers, 1980, Murine Mammary Tumor Virus, in, Viral Oncology, Klein, G. ed., Raven Press, N.Y., pp. 311–355). These murine mammary tumor viruses are retroviruses that do not themselves carry an oncogene, but are thought to cause tumors by insertion of the viral promoter or enhancer sequences near a cellular protooncogene resulting in activation of the oncogene and transformation of the cell (see, Darnell et al., 1986, Molecular Cell Biology, W. H. Freeman & Company, N.Y., pp.1051–1063). In the examples discussed infra digoxin was administered to these mice continuously from the time they were two to three months old; thus the mice were treated with digoxin at a time that was probably subsequent to infection but prior to transformation by the virus. It may be that the digoxin successfully inhibited activation and expression of the responsible oncogene due to the ability of digoxin to inhibit the membrane bound $Na^+$, $K^+$-ATPase which alters the ionic flux of the cell membrane.

Notably, the reduced products of the cardiac glycosides were not efficacious in preventing tumor development. How can this pharmacokinetic difference between these two very similar products be explained? A possible mechanism may be that both digoxin and dihydrodigoxin compete for the same membrane cellular receptor sites. It appears that the reduced products are taken up less avidly by the receptor sites of cardiac muscle than digoxin (Marcus F. I., et al., 1975, J. Lab. Clin. Med., 85: 610–620; Flasch H., et al., 1978, Naunyn Schmiedebergs. Arch. Pharmacol., 304: 37–44; Heinz N., et al., 1978, Naunyn Schmiedebergs. Arch. Pharmacol., 303: 181–187). The affinity of both digoxin and dihydrodigoxin for receptor sites of other cells of the body has not been extensively studied. Once the receptor sites are saturated with either of these two products they may not be available to the other. Although the affinity of these receptor sites to digoxin and dihydrodigoxin may be different, the ability of either one to displace the other once it is bound, has not been extensively studied. Apparently, the reduced products of digoxin, although having the capability to bind to membrane cellular receptor sites, have minimal or no inhibitory effect on $Na^+,K^+$-ATPase, thereby resulting in minimal or no change in transmembrane potential.

Consequently, from these experiments described infra, one can conclude that an effective method to prevent neoplasia, specifically, mammary tumors, can be achieved by administering digoxin. All the appropriate receptor sites must be bound to digoxin, and not one of its reduced products, prior to, and during exposure to an oncogenic virus, ionizing radiation, or chemical carcinogen. If it is determined that the individual has anaerobes capable of reducing digoxin, these should be eradicated with an appropriate antibiotic or other therapy.

The method of the invention is described in more detail in the subsections which follow.

4.1. Choice Of Cardiac Glycoside, Treatment And Dosage

Any cardiac glycoside derived from natural sources or synthetically produced may be used in accordance with the method of the present invention, including, but not limited to digitoxin, digitalis, gitalin, digoxin, digitoxin, lanatoside C, deslanoside, acetyldigitoxin, ouabain as well as pharmaceutically active derivatives thereof including, but not limited to beta-methyldigoxin. The cardenolides including, but not limited to digoxin, digitoxin, or beta-methyldigoxin, which are in predominant clinical use are preferred.

The cardiac glycosides can be administered by any route, including but not limited to oral, intravenous, intramuscular, transcutaneous and transdermal modes of administration, although the oral route is currently preferred.

By tradition, the initial dose of a cardiac glycoside is called the digitalizing dose which is followed by maintenance doses. The doses should be adjusted to maintain a therapeutic plasma concentration up to about 2.5 ng/ml for digoxin or about 9 to 35 ng/ml for digitoxin.

4.2. Identifying Patients With A High Risk Of Developing Cancer

Individuals at a high risk of developing cancer should be selected for treatment in accordance with the invention. Different cancers are associated with different risk factors which should be assessed in order to identify which individuals should receive prophylactic treatment with cardiac glycosides. Table I below lists some of the major cancer sites and their associated risk factors as identified by the American Cancer Society.

TABLE I

Risk Factors Associated With Different Cancers

| CANCER | RISK |
| --- | --- |
| Lung | Cigarette smoking; history of smoking 20 or more years; exposure to certain industrial substances such as asbestos, particularly for those who smoke. |
| Colorectal | Personal or family history of colon and rectum cancer; personal or family history of polyps in colon or rectum; inflammatory bowel disease. Evidence suggests that bowel cancer may be linked to the diet. A diet high in fat and/or deficient in fiber content may be a significant causative factor. |
| Breast | Over age 50; personal or family history of breast cancer; never had children; first child after age 30. |
| Skin | Excessive exposure to sun; fair complexion; occupational exposure to coaltar, pitch, creosite, arsenic compounds or radium. Among blacks, because of heavy skin pigmentation, skin cancer is negligible. |
| Uterine | Cervical Cancer: early age at first intercourse, multiple sex partners. Endometrical cancer: history of infertility, failure of ovulation, prolonged estrogen therapy and obesity. |

The present invention is not limited to the use of the above-identified factors for assessing an individual's risk of developing cancer. As more risk factors are identified it will become apparent to the skilled artisan to utilize the newly identified factors in order to evaluate and identify the individuals who may require treatment in accordance with the invention. In this regard, it is contemplated that the emerging and progressive use of molecular biological techniques in diagnostics may lead to the development of assays that are predictive rather than diagnostic for cancer. For example, nucleotide hybridization assays for the detection of marker genes or immunoassays for the detection marker gene products, proteins, lipids, carbohydrates, factors, intermediates and the like, that are predictive of whether an individual will develop cancer are likely to be researched and developed. Such predictive assays may be utilized by the skilled artisan to assess the patient's risk of developing cancer, and the use of such tests to identify individuals who may require treatment with cardiac glycosides to prevent neoplasms is considered to be within the scope of the present invention.

4.3. Identification And Treatment Of Converters

As previously explained, a few individuals form cardio-inactive metabolites of digoxin which appear to be made by bacteria in the gastrointestinal tract, probably the colon. Such conversion cannot be avoided by non-oral routes of administration due to secretion of the drug into the gastrointestinal tract via the entero-hepatic circulation, conversion of the drug to a cardioinactive metabolite and reabsorption and entry of the metabolite into the systemic circulation. As exemplified by the murine model disclosed herein, these reduced metabolites are not effective in the prevention of neoplasms; therefore in the preferred embodiment of the invention, the individual at risk of cancer should be tested to determine whether the individual converts the cardiac glycoside to its inactive reduced form. Such tests include, but are not limited to testing stool cultures from the subject for the ability of the cultured microorganisms to convert cardiac glycosides to their reduction products. Certain strains of *Eubacterium lentum*, a common anaerobe of the human colonic flora, have been identified in the bioconversion of digoxin to its reduced derivatives (Dobkin et al., 1982, Science 220: 325–327). Alternatively, urinary, stool or serum samples of such individuals may be assayed for the presence of cardiac glycoside reduced products; such assays include but are not limited to immunoassays using antibodies that identify the reduced inactive metabolites yet do not cross react with the unaltered active drug. (For descriptions of some assays which may be used, see Lindenbaum, et al., 1981, The Amer. J. Med. 71: 67–74; Lindenbaum, et al., 1981, N. Engl. J. Med. 305: 789–794; Dobkin et al., 1982, Science 220: 325–327; Marcus, et al., 1985, J. Am. Coll. Cardiol. 5: 82A–90A; Soldin, 1986, Clin. Chem. 32/1: 5–12).

If an individual at high risk of developing cancer has been identified as a converter, the cardiac glycoside should be administered using a regimen or preparation that either minimizes or eliminates the biotransformation of the drug to an inactive metabolite. Such methods include, but are not limited to the administration of the cardiac glycoside in conjunction with certain antibiotic therapies which cause disappearance of the reduced metabolites from the stool and urine and lead to an increased bioavailability of the drug. Antibiotic therapy using erythromycin, clindamycin or tetracycline was found to increase serum digoxin concentrations in cardiac patients who produced large amounts of reduced digoxin products (Lindenbaum, et al., 1981, Engl. J. Med. 305: 789–794). Thus, antibiotic therapy using a tetracycline or a macrolide antibiotic including but not limited to erythromycin and clindamycin could be used in conjunction with the prophylactic administration of cardiac glycosides to prevent neoplasms in accordance with the invention. Alternatively, administration of cardiac glycosides in a capsule form such as Lanoxicaps® (Burroughs Wellcome, N.C.) which allows more complete absorption in the small intestine can decrease the percent of reduction products formed (see, Rund, et al., 1983, Clin. Pharmacol. Ther. 34: 738–743; and Marcus, 1985, J. Am. Coll. Cardiol. 5: 82A–90A). Another method for eliminating the biotransformation of cardiac glycosides in individuals may involve inhibiting the bioconversion effected by colonic anaerobes rather than killing the anaerobes. For example, high concentrations of arginine have been reported to inhibit the bioconversion of digoxin by *Eubacterium lentum* cultures in vitro and therefore, it is conceivable that high concentrations of arginine in the lower gastrointestinal tract may inhibit bioconversion in vivo (Dobkin, et al., 1982, Science 220: 325–327).

5. EXAMPLE: PREVENTION OF NEOPLASIA BY THE ADMINISTRATION OF DIGOXIN

In the examples that follow, a murine model is used to demonstrate the prevention of neoplasms in vivo by treatment with digoxin. The experiments described also reveal that the reduced form of digoxin, dihydrodigoxin, was not effective in the prophylaxis of tumors. Moreover, digoxin was ineffective in animals which converted digoxin to its reduced from, dihydrodigoxin.

5.1. Treatment of Mice

Four groups of inbred mice which spontaneously develop mammary tumors were treated as follows:

Group A consisted of twenty-two C3H (Bittner) female mice with an incidence of about forty percent spontaneous mammary tumors, at the time of the experiment. These animals were inbred at the Cancer Research Unit of the Bronx Medical Center for about forty years. The mice were two to three months of age at the onset of the experiment. Eleven females were treated with digoxin orally as follows: 2cc Digoxin Injection, U.S.P. (a sterile solution of 0.25 mg/ml digoxin in 10% alcohol) was added to 98cc drinking water which the animals were permitted to drink ad lib. Eleven litter mates of similar age were used as controls which received identical treatment but no drug.

Group B consisted of twenty-four C3H/d (Dmochowski) substrain females also inbred at the Cancer Research Unit, Bronx Medical Center since 1965. The average incidence of spontaneous tumors in that strain of mice at the time of the experiment was seventy-three percent. Twelve females, two to three months old were treated with digoxin orally as described for group A; i.e., 2cc Digoxin Injection, U.S.P. was added to 98cc drinking water which the animals were permitted to drink ad lib. Twelve litter mates, of similar age were used as controls which received identical treatment but no drug.

Group C consisted of seventy-nine C3H/OUJ mice purchased from Jackson Laboratory in Bar Harbor in 1983. Forty females (average age two months) were treated with digoxin as described above; i.e., 2cc Digoxin Injection, U.S.P. was added to 98cc drinking water which the animals drank ad lib. Thirty-nine females from the divided litters were used as controls and received no drug.

Group D consisted of eight-three C3H/OUJ females bred from animals bought at Bar Harbor. They were two months old when used for this experiment. Thirty-one were treated with dihydrodigoxin crystals dissolved in their drinking water (a final concentration of about 2 ug/ml). The bottles containing the drinking water and dihydrodigoxin crystals were shaken frequently in order to insure maximum solubility of the crystals. The animals were allowed to drink ad lib. Fifty-two females of the same age were used as controls and received no drug.

All the animals in each group were fed Purina Lab Chow and oats. They were checked biweekly for evidence of tumors. When tumors appeared, the animals were sacrificed, weighed, and blood was taken to check the serum digoxin level using a radioimmunoassay (RIA) method (Ventrex Coated Tube RIA-digoxin assay; Butler, 1967, Proc. Natl. Acad. Sci. 57: 71–78; Butler, 1972, Progr. of Cardiovasc. Diseases 14: 571). Sections of the tumors were taken for analysis by both light microscopy and estrogen, progesterone receptor determination. When autopsies were performed, other abnormalities, if present, were noted.

Random stool cultures were taken from litter mates of C3H, C3H/d and C3H/OUJ mice not part of either the control or experimental group, but given a similar diet and under similar living conditions. These were obtained by sacrificing the animal, incising the large intestine and removing its content aseptically for culture.

In order to identify strains of experimental mice which are "converters" (i.e., those strains which reduce digoxin to its inactive dihydrodigoxin form), offspring of the C3H, C3H/d and C3H/OUJ strains of mice, not part of previous groups, were given oral digoxin in the same dosage as groups A, B, and C. Urine samples obtained from these mice were assayed for the presence of dihydrodigoxin using an enzyme-linked immunosorbent assay (ELISA) in which an antibody specific for dihydrodigoxin but not cross-reactive with digoxin was used. As a control group, urine samples of litter mates of these strains of mice which were not given oral digoxin were similarly assayed for dihydrodigoxin.

5.2. Results Of Treatment.

The results of experiments described above are presented in Table II and discussed in more detail below.

TABLE II

PREVENTION OF MAMMARY TUMORS IN MICE BY TREATMENT WITH DIGOXIN

| Strain | Digoxin Converter (+ or −)* | Development of Mammary Tumors In Mice Treated With: | | | |
|---|---|---|---|---|---|
| | | Digoxin** | | Untreated | |
| | | Ratio | % | Ratio | % |
| C3H | − | 0/11 | 0 | 8/11 | 73 |
| C3H/d | − | 0/12 | 0 | 8/12 | 67 |
| C3H/OUJ | + | 34/40 | 85 | 36/39 | 92 |

| | | Dihydro-Digoxin*** | | Untreated | |
|---|---|---|---|---|---|
| | | Ratio | % | Ratio | % |
| C3H/OUJ | + | 26/31 | 84 | 47/52 | 90 |

Identification of a mouse strain as a converter (+) of digoxin to inactive dihydrodigoxin was based upon two criteria: (1) the detection of high levels of dihydrodigoxin in urine samples of litter mates treated with digoxin (as assayed by ELISA, concentrations of about 2 ng/ml were measured in nonconverters whereas concentrations greater than 300 ng/ml were detected in converters); and (2) the identification of digoxin-reducing anaerobic bacteria in stool samples cultured from litter mates.
**Two to three month old female mice were treated with oral doses of digoxin as follows: 2 cc Digoxin Injection, U.S.P. (a sterile solution of 0.25 mg/ml digoxin in 10% alcohol) was added to 98 cc drinking water which the animals were permitted to drink ad lib.
***Two to three month old female mice were treated with oral doses of dihydrodigoxin as follows: a saturating amount of dihydrodigoxin was dissolved in their drinking water resulting in a final concentration of about 2 ug/ml; the animals were permitted to drink ad lib.

In group A, none of the eleven treated C3H female mice developed tumors. In the eleven female controls, eight developed spontaneous mammary tumors, seven of which were histologically determined to be adenocarcinoma and one was benign. The age of onset varied from seven to sixteen months. The spontaneous incidence of tumors in this strain of mice was seventy-three percent.

In group B, none of the twelve C3H/d females treated mice developed tumors. In the control group of twelve, eight developed spontaneous mammary tumors. All were determined to be adenocarcinoma. The age of onset of tumors varied from nine and a half to eleven months. The spontaneous incidence of tumors in this strain was sixty-seven percent.

In group C, of the forty female treated C3H/OUJ mice, thirty-four or eight-five percent developed mammary tumors. The average age of onset was thirteen months; the spread was from seven to twenty-two months. In the control group of thirty-nine C3H/OUJ females, thirty-six or ninety-four percent developed spontaneous tumors. Age of onset varied between six and a half and twenty-one months. All tumors in both the treated and control groups were determined to be adenocarcinomas.

In group D, of the thirty-one treated C3H/OUJ female mice, twenty-six or eighty-four percent developed mammary tumors. The average age of onset was thirteen months, varying from six and a half to twenty and a half months. In the control group of fifty-two C3H/OUJ females, forty-seven or ninety percent developed spontaneous mammary tumors. The average age of onset was fourteen months, with a range from six to twenty-one months. All tumors examined by light microscopy in the treated and control groups were adenocarcinomas.

In all four groups, random blood digoxin determinations were done at the time of death using a radioimmunoassay employing an antibody that defines digoxin but cross reacts with dihydrodigoxin; serum levels varied between 6 to 10 ng/ml. Because of the cross-reactivity of the antibody used in the immunoassay, elevated blood levels were also noted in group D where the animals received dihydrodigoxin instead of digoxin in their drinking water. No difference in weight, at the time of death, was noted between the treated and control groups.

All neoplasms tested for estrogen, progesterone receptor were reported as "negative". These were tumors from all four groups.

A difference in stool culture was noted between the C3H, C3H/d and C3H/OUJ mice. The significantly high preponderance of anaerobes in the C3H/OUJ group was confirmed in all specimens tested.

Extremely high levels (over 300 ng/ml) of dihydrodigoxin were detected on all urines tested from treated mice of the C3H/OUJ strain. Minimal amounts of dihydrodigoxin (about 2 ng/ml) were detected in the treated C3H and C3H/d strain. None was detected in the control group.

The results obtained in group A and group B demonstrate the ability of digoxin to totally prevent mammary tumors in a highly susceptible strain of female mice. Of the twenty-three female mice, eleven C3H (Bittner) strain (group A) and twelve of the C3H/d (Dmochowski) substrain that were treated with digoxin in their drinking water from two to three months of age, none of the animals developed mammary or any form of neoplasm. In the control group of twenty-three female mice, eight out of eleven mice in group A and eight out of twelve in group B developed spontaneous tumors. The difference in the incidence of spontaneous tumors in the control groups A and B, which was about seventy percent, as compared to a zero incidence in the treated groups A and B, is impressive and highly significant statistically (p less than 0.0024). In group C, consisting of forty treated and thirty-nine controls C3H/OUJ strain female mice, the results, however, clearly indicated no such protective effect against mammary tumors by digoxin. The incidence of mammary tumors in the treated group was eighty-five percent as compared to ninety-four percent in the control group.

The data presented above demonstrates that the administration and maintenance of an effective dose of the cardiac glycoside, digoxin, in its pharmacologically active unreduced form completely prevented the development of neoplasms in vivo in a genetically susceptible strain of mammal.

The present invention is not to be limited in scope by the embodiment disclosed in the examples which is intended as a single illustration of one aspect of the invention and any methods which are functionally equivalent are within the scope of this invention. Indeed, various modifications of the invention in addition to those shown and described herein will become apparent to those skilled in the art from the foregoing description. Such modifications are intended to fall within the scope of the appended claims.

What is claimed is:

1. A method for preventing murine or human mammary tumors in vivo, comprising administering to a murine or human subject who (a) is at an increased risk of developing mammary tumors and (b) does not convert cardiac glycosides to reduced inactive metabolites, a therapeutically effective dose of a cardiac glycoside so that the cardiac glycoside is maintained at a therapeutically effective concentration in its unreduced form in the subject's serum prior to and during the transforming event that causes the mammary tumor.

2. The method according to claim 1 in which the cardiac glycoside is a cardenolide.

3. The method according to claim 1 in which the cardiac glycoside is a bufadienolide.

4. The method according to claim 2 in which the cardenolide is a digitalis glycoside.

5. The method according to claim 4 in which the digitalis glycoside is digoxin.

6. The method according to claim 4 in which the digitalis glycoside is digitoxin.

7. The method according to claim 5 in which the digoxin is maintained at a serum concentration of up to about 2.5 ng/ml.

8. The method according to claim 6 in which the digitoxin is maintained at a serum concentration of about 9 ng/ml to about 35 ng/ml.

9. The method according to claim 1 in which the cardiac glycoside is beta-methyldigoxin.

10. The method according to claim 2 in which the cardenolide is a strophanthidine.

11. The method according to claim 10 in which the strophanthidine is ouabain.

12. The method according to claim 1, 2, 3, or 4 in which the cardiac glycoside is administered orally.

13. The method according to claim 1, 2, 3 or 4 in which the cardiac glycoside is administered transcutaneously.

14. The method according to claim 1, 2, 3 or 4 in which the cardiac glycoside is administered intravenously.

15. The method according to claim 1, 2, 3 or 4 in which the cardiac glycoside is administered transdermally.

16. A method for preventing murine or human mammary tumors in vivo, comprising administering to a murine or human subject who (a) is at an increased risk of developing mammary tumors and (b) converts cardiac glycosides to reduced inactive metabolites via intestinal anaerobic bacteria, a therapeutically effective dose of a cardiac glycoside and a second drug that inhibits bacterial conversion so that the cardiac glycoside is maintained at a therapeutically effective concentration in its unreduced form in the subject's serum prior to and during the transforming event that causes the mammary tumor.

17. The method according to claim 16 in which the cardiac glycoside is a cardenolide.

18. The method according to claim 16 in which the cardiac glycoside is a bufadienolide.

19. The method according to claim 17 in which the cardenolide is a digitalis glycoside.

20. The method according to claim 19 in which the digitalis glycoside is digoxin.

21. The method according to claim 16, 17, 18, 19 or 20 in which the second drug is an antimicrobial agent.

22. The method according to claim 21 in which the antimicrobial agent is a macrolide antibiotic.

23. The method according to claim 22 in which the macrolide antibiotic is erythromycin.

24. The method according to claim 22 in which the macrolide antibiotic is clindamycin.

25. The method according to claim 21 in which the antimicrobial agent is a tetracycline.

26. The method according to claim 16 in which the cardiac glycoside is administered orally.

27. The method according to claim 16 in which the cardiac glycoside is administered transcutaneously.

28. The method according to claim 16 in which the cardiac glycoside is administered intravenously.

29. The method according to claim 16 in which the cardiac glycoside is administered transdermally.

30. A method for preventing murine or human mammary tumors in vivo, comprising administering to a murine or human subject who (a) is at an increased risk of developing mammary tumors and (b) converts cardiac glycosides to inactive metabolites via intestinal anaerobic bacteria, a therapeutically effective dose of a cardiac glycoside administered orally in a capsule form which allows more complete absorption in the small intestine in order to decrease bacterial conversion so that the cardiac glycoside is maintained in its unreduced form in the subject's serum prior to and during the transforming event that causes the mammary tumor.

31. The method according to claim 30 in which the cardiac glycoside is a cardenolide.

32. The method according to claim 30 in which the cardiac glycoside is a bufadienolide.

33. The method according to claim 31 in which the cardenolide is a digitalis glycoside.

* * * * *

UNITED STATES PATENT AND TRADEMARK OFFICE
CERTIFICATE OF CORRECTION

PATENT NO. : 5,872,103

DATED : February 16, 1999

INVENTOR(S) : Dino A. Belletti

It is certified that error appears in the above-indentified patent and that said Letters Patent is hereby corrected as shown below:

Title page, under "References Cited" section [56], the heading entitled "PUBLICATIONS" should be deleted and inserted in its place --U.S. PATENT DOCUMENTS

| | | |
|---|---|---|
| 4,067,960 | 1/1978 | Fadda..........514/26 |
| 4,088,750 | 5/1978 | Gressnell et al.........514/26 |

OTHER PUBLICATIONS--

Additionally, after "Li et al., *Chemical Abstract*, Vol. 88(1) 1978, p.15 No. 166a" contained is the newly inserted heading "OTHER PUBLICATIONS", the citations to the following references of record should be inserted:

--Goldin and Safa, 1984, *The Lancet*, May 19, page 1134
Lindenbaum et al., 1981, *The New England Journal of Medicine*, 305:789-794
Lindenbaum et al., 1981, *The American Journal of Medicine*, 71:67-74
Dobkin et al., 1983, *Science*, 220:325-327
Rund et al., 1983, *Clin. Pharmacal. Ther.*, 34(6):738-743
Friedman, 1984 *The Lancet*, October 14, page 875
Shiratori, 1967, GANN 58:521-528
Williams et al., 1976, *Am. J. Med. Sci.*, 272(2):132-137
Stenkvist et al., 1979, *Analyt. Quant. Cytol.*, 2:49-54
Stenkvist et al., 1979, *The Lancet*, March 10, p. 563
Stenkvist et al., 1982, *The New Engl. J. Med.*, Feb. 25, p. 484
LeWinn, 1979, *The Lancet*, June 2, pp. 1196-1197
Cove and Barker, 1979, *The Lancet*, July 28, p. 204
Falconer et al., 1983, *Chemotherapy*, 29: 368-372
Goodman and Gilman, eds., 1980, *The Pharmacological Basis Of Therapeutics*, 6th Edition, Ch. 30, pp. 729-760

UNITED STATES PATENT AND TRADEMARK OFFICE
CERTIFICATE OF CORRECTION

PATENT NO. : 5,872,103
DATED : February 16, 1999
INVENTOR(S) : Dino A. Belletti

It is certified that error appears in the above-indentified patent and that said Letters Patent is hereby corrected as shown below:

Butler, 1967, *Proc. Natl. Acad. Sci.*, 57:71-78
Butler, 1972, *Progr. of Cardiovasc. Diseases*, 14:571
Marcus et al., 1975, *J. Lab. Clin. Med.*, 85:610-620
Flasch et al., 1978, *Naunyn. Schmiedebergs. Arch. Pharmacol.*, 304:37-44
Heinz et al., 1978, *Naunyn. Schmiedeberges. Arch. Pharmacol.*, 303:181-187
Marcus, 1985, *J. Am. Coll. Cardiol.*, 5(5): 82A-90A
Cancer Facts and Figures, 1986, The American Cancer Society
Bentvelzen and Hilgers, 1980, Murine Mammary Tumor Viruses, in Viral Oncology, Klein, G., ed., Raven Press, NY pp. 311-355
Darnell et al., *Molecular Cell Biology*, 1986, W.H. Freeman & Co., N.Y., pp. 1051-1063
Morgan and Curran, 1986, *Nature*, 322:552-555
Soldin, 1986, *Clin. Chem.*, 32(1):5-12 --

Signed and Sealed this

Nineteenth Day of October, 1999

Q. TODD DICKINSON

*Attest:*

*Attesting Officer*    *Acting Commissioner of Patents and Trademarks*